United States Patent [19]
Panchaud

[11] Patent Number: 5,811,092
[45] Date of Patent: Sep. 22, 1998

[54] NEMATOPHAGE AGENT AGAINST NEMATODES OF THE MELOIDOGYNE GENUS

[75] Inventor: Elisabeth Panchaud, Antibes, France

[73] Assignee: IDRO 2000 S.A., Biasca, Switzerland

[21] Appl. No.: 750,655

[22] PCT Filed: Jun. 14, 1995

[86] PCT No.: PCT/FR95/00785

§ 371 Date: Dec. 16, 1996

§ 102(e) Date: Dec. 16, 1996

[87] PCT Pub. No.: WO95/34209

PCT Pub. Date: Dec. 21, 1995

[30] Foreign Application Priority Data

Jun. 15, 1994 [FR] France ................................ 94 07553

[51] Int. Cl.$^6$ .................................................. A01N 63/00
[52] U.S. Cl. .................. 424/93.5; 424/405; 424/93.1; 424/93.21; 424/93.3; 424/93.51; 435/254.1; 435/911
[58] Field of Search .................. 424/405, 93.1, 424/93.21, 93.3, 93.5, 93.51; 435/254.1, 911

[56] References Cited

U.S. PATENT DOCUMENTS

| | | | |
|---|---|---|---|
| 4,421,544 | 12/1983 | Jones et al. | 71/7 |
| 4,666,714 | 5/1987 | Cayrol | 424/93.5 |

FOREIGN PATENT DOCUMENTS 0006382  9/1980  European Pat. Off. .

OTHER PUBLICATIONS

Database Biosis, Biosciences Information Service, Philadelphia, PA, Abstract No. 74:42115, Al–Hazmi A S et al., "The Effect of Arthrobotrys–Conoides on Meloidogyne–Incognita Population Densities in Corn as Influenced by Temperature Fungus Inoculum Density and Time of Fungus Introduction in the Soil".

Database Biosis, Biosciences, Information Service, Philadelphia, PA, Abstract No. 88:78086, Kim H K et al. "Decrease of Nematode Population by Introduction of Nematophagous Fungi into the soil as affected by inoculum Concentration and Temperature In–vitro".

Chemical Abstracts, vol. 85, No. 19, 1976, Columbus, OH: Abstract No 138578; S. DIBS "Side–effects of Systemic Fungicides of Systemic Fungicides on Plant–Parasitic Nematodes and Nematode–Tapping Fungi".

ATCC Catalog, Jong et al. (eds.) 1987 American Type Culture Collection, Rockville, MD. pp. xii and 24.

*Primary Examiner*—Christopher S. F. Low
*Attorney, Agent, or Firm*—Ostrolenk, Faber, Gerb & Soffen, LLP

[57] ABSTRACT

Nematophage agent intended to combat nematodes of the *Meloidogyne, Heterodera* and *Ditylenchus Myceliophagus* genus, characterised in that it is selected within a group of six strains of *Arthrobotrys conoides* Drechsler (42A, 42A', 42B, 42Br, 42T and 42VI), deposited at the national collection of cultures of micro-organism (Institut Pasteur) under the numbers I-1425 to I-1430, and application process consisting in incorporating the nematophage agent into the ground wherein the cultures are grown by means of grains which have been seeded previously with the inoculum of the nematophage agent.

12 Claims, 1 Drawing Sheet

NEMATOPHAGE AGENT AGAINST NEMATODES OF THE MELOIDOGYNE GENUS

This application is a 35U.S.C.371 filing of PCT/FR95/00785 filed 14 Jun. 1995.

TECHNICAL FIELD

The present invention relates to a new nematophagous agent intended to combat nematodes of the *Meloidogyne* genus, and a process to combat the proliferation of these nematodes, by utilizing new strains of the mushroom *Arthrobotrys conoides* Drechsler.

STATE OF THE ART

It has been known for long that phytophagous nematodes cause an important loss, valued at three billion francs per year, to cultures. The most widespread species, causing the most important loss around the world belong to the *Meloidogyne* genus. Indeed, this genus, better known as <<gall nematodes >> among farmers, is responsible for the formation of galls on the radicular system of the infected plants. These extremely polyphagous nematodes attack almost any culture, and are thus responsible for disastrous yield loss, in the order of 50 to 70%.

In many areas, *Heteodera carotae* specifically causes damage to carrot cultures, insofar as its stings release an abnormal production of lateral rootlets on carrots, which become unmarketable.

Another nematode, *Ditylenchus myceliophagus*, causes important damage to the surgeous agaric in mushroom beds.

To combat these nuisances, farmers have several means available, which, in intensive farming, come down to:
- a preventive soil disinfection before cultivation, with fumigants (methyl bromide, trichloronitromethane, dichloropropene. . . ). These products, which have a very broad efficiency spectrum, sterilize the soil and destroy the ecological balance. Moreover, in light soils, their residue may end up in the ground water, and in heavy soils, their efficiency decreases because of low diffusion.
- or some curing treatments on some cultures in situ, by means of systemic products conveyed by the sap (carbamates or oligophosphorous elements) for inedible productions, such as floral cultures or tree nurseries. These products are dangerous for both animals and humans as they get into the plant and leave some toxic remnants in it.

Both techniques only affect the first thirty centimeters of soil. Nevertheless, nematodes living at a greater depth will infect the cured area again during the culture to come. It implies never-ending disinfections.

Moreover, as they are toxic to humans, several nematode killing chemicals are forbidden in many countries, such as Netherlands, Switzerland, Germany.

OVERVIEW OF THE INVENTION

Therefore, the object of the invention is to use a natural nematode combating agent, harmless to men and to their environment.

Therefore, the invention relates to a new nematophagous agent intended to combat nematodes of the *Meloidogyne, Heterodera* and *Ditylenchus myceliophagus* genus, chosen among six strains of the *Arthrobotrys conoides* Dreschler mushroom.

Another aspect of the invention is a process to combat nematodes of the *Meloidogyne, Heterodera* and *Ditylenchus myceliophagus* genus, consisting in blending the *Arthrobotrys conoides* Dreschler mushroom to the cultivation soil by means of grains previously seeded with the mushroom inoculum.

BRIEF DESCRIPTION OF THE DRAWINGS

The objects and characteristics of the present invention are presented in the following description, in connection with the attached drawings, illustrating some aspects of the invention.

DETAILED DESCRIPTION OF THE INVENTION

The six strains of *Arthrobotrys conoides* Dreschler, subject of the invention, come from different places. The main criterion to check whether the different strains belong to the same species is the measurement of the conidia (reproduction organs of these mushrooms).

Figure 1:
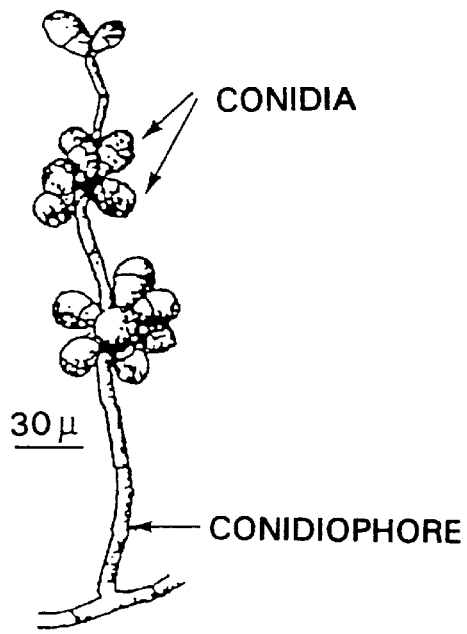
FIG. 1 schematically presents a conidiophore and the conidia of the strains *Arthrobotrys conoides*, according to the invention.

As illustrated on FIG. 1, the conidia are gathered in groups of 20 or 30 on a conidiophore. The conidiophores may develop further after a first conidia head and form a second group of conidia after a certain growth length and so on, till 5 to 6 additional groups are developed.

Strain 42A comes from Fada N'Gourma in Burkina Faso, and is made of a mycelium consisting of compartmentalized glass-like hyphae.

The conidiophores end up in a head of about 20 tight conidia; on old cultures, they carry on developing and may successively produce 5 to 10 additional groups of conidia.

The conidia are considerably thinner towards their base, they are almost cone shaped and made of two cells of different sizes, the total mean length is 27 $\mu$m.

This strain was deposited at the National Collection of Micro-organism Cultures (CNCM), at the Institut Pasteur, under number I-1425.

Strain 42A' comes from Leguema in Burkina Faso.

The conidiophores end up in a head of 3 to 20 tight conidia; on old cultures, they carry on developing and may successively produce 3 to 5 additional groups of conidia.

The conidia are considerably thinner towards their base, they are almost cone shaped and made of two cells of different sizes, the total mean length is 30 $\mu$m.

This strain was deposited at the CNCM (Institut Pasteur), under number I-1426.

Strain 42B comes from Baarn Mushroom Collection in the Netherlands.

On young cultures (less than one month old), the conidiophores are rare and end up in a head of 3 to 20 tight conidia; the formation of additional groups of conidia is rare.

The conidia are considerably thinner towards their base, they are almost cone shaped and made of two cells of different sizes, the total mean length is 28 $\mu$m.

This strain was deposited at the CNCM (Institut Pasteur), under number I-1427.

Strain 42Br comes from Brazil.

The conidiophores end up in a head of 10 to 20 tight conidia. They carry on developing and successively produce 5 to 10 additional groups of conidia.

The conidia are considerably thinner towards their base, they are almost have cone shaped and made of two cells of different sizes, the total mean length is 23 µm.

This strain was deposited at the CNCM (Institut Pasteur), under number I-1428.

Strain 42T was collected at Tours Indre-et-Loire (France).

The conidiophores end up in a head of 10 to 20 tight conidia. On old cultures, they carry on developing and successively produce 3 to 5 additional groups of conidia.

The conidia are considerably thinner towards their base, they are almost cone shaped and made of two cells of different sizes, the total mean length is 28 µm.

This strain was deposited at the CNCM (Institut Pasteur), under number I-1429.

Strain 42Vl was collected at Villeneuve Loubet Alpes-Maritimes (France).

The conidiophores end up in a head of 10 to 20 tight conidia. On old cultures, they carry on developing and successively produce 20 to 30 additional groups of conidia.

The conidia are considerably thinner towards their base, they are almost cone shaped and made of two cells of different sizes, the total mean length is 23 µm.

This strain was deposited at the CNCM (Institut Pasteur), under number I-1430.

Figure 2:
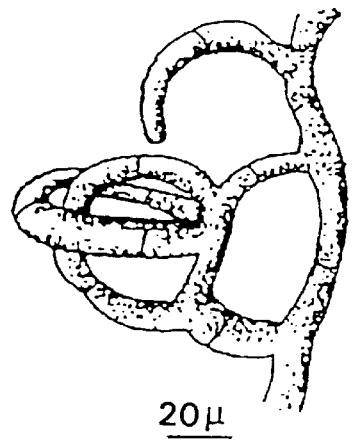
FIG. 2 is a schematic representation of the traps formed by the strains *Arthrobotrys conoides* according to the invention, to catch nematodes.

The mycelium of nematophagous mushrooms has the capacity of producing catching organs which trap nematodes. The traps of the mycelium of the six *Arthrobotrys conoides* strains according to the invention have the shape of hyphal loops which transform themselves in more or less intricate networks through anastomosis, as illustrated on FIG. 2.

Among the six strains studied, only strain 42A spontaneously forms traps. For the five others, the presence of nematodes within the growing medium induces the formation of traps. In both cases, the traps consist of hyphal loops which are transformed through anastomosis in more or less intricate networks.

The six strains can be undoubtedly differentiated thanks to an oligonucleotide revealed in the genome study with the RAPD technique.

Figure 3:
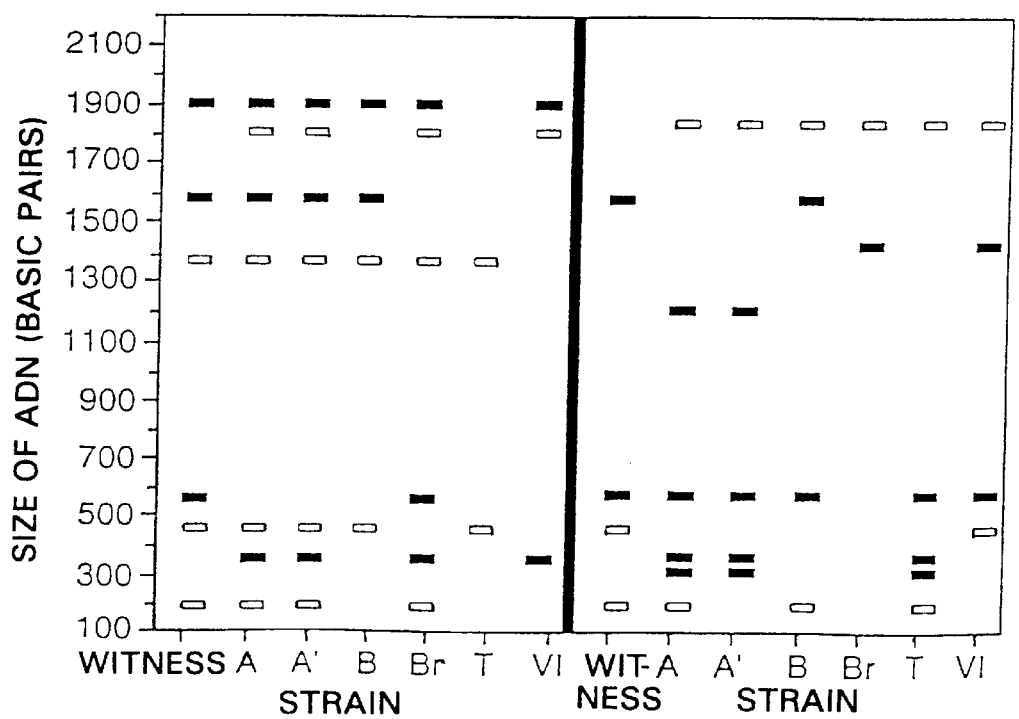
FIG. 3 is a table of the results obtained with a electrophoresis gel used to differentiate the different strains of *Arthrobotrys conoides*.

The use of an electrophoresis gel leads to the results on FIG. 3, on which the bands have been schematized and for which the reference is employed to size the DNA fragments.

The different strains of *Arthrobotrys conoides* may be used industrially to combat nematodes, by processing as described below.

To preserve the mushroom in good conditions, a grain-based growing medium is used. The mushroom shelters inside the grain and thus becomes less sensitive to external attacks. Moreover, each grain spread on the ground is the starting point of a new mycelian colony.

The grains are dipped in water in excess for 24 hours, before being sterilized. The grains are then seeded with the mushroom inoculum.

The best species to use for support allow for a maximum growth in the shortest length of time. A second criterion is the number of propagation units per gram reached at the growth apex. The propagation unit corresponds to a minimum mycelium fragment or even to a sole conidium.

The species that may be used are chosen among the grass, leguminous or oleaginous plants. Thus, hamp, sunflower and rice for which the time to reach maximum growth is 14 days, may be used. Oat, sorghum, barley, wheat, lentil, corn, alpist, soya, bean, lupin, chick pea, horse bean may also be used.

Among the above species, the maximum number of propagation units, about $3.10^7/g$, is reached with lupin, lentil, corn, bean, alpist, chick pea and rice.

For a better distribution of the mushroom, it is recommended, at equal weight, to spread small grains. Because of this and for other reasons, alpist, lentil and corn are preferably used. For corn, the rate of 2 g per liter soil allows for a satisfactory blending.

As some time is required to reach the growth apex, it is recommended to blend the mushroom and its support about 15 days before planting.

The different strains of *Arthrobotrys conoides* can also be used in the form of a freeze-dried product. It is here reminded that freeze-drying is a technique of desiccation by sublimation of the ice contained in solutions or suspensions of tissues, which had previously been solidified by freezing. This technique is commonly used for preserving microorganisms in National Mushroom Collections. It implies a strict respect of the operating conditions:

low temperature to ensure the freezing of the product, low pressure to ensure the sublimation of ice absence of interstitial liquid during ice sublimation.

To fulfill these conditions, there is just to create an imbalance between the pressure and the temperature of the product to freeze-dry, by rising the temperature while evacuating the vapor. Freeze-drying mushrooms cannot be done on mycelium, which is too sensitive to temperature and pressure variations. So the mushroom has to multiply, in order to obtain conidia behaving as resistance organs that can undergo freeze-drying. The necessity of employing conidia eliminates the use of any liquid medium in the same time. The mushroom is grown on an agar-agar soya-flour-based medium.

To eliminate the disadvantage brought by the presence of agar-agar and by the weight of the culture medium (soya flour), a cellophane film is inserted between the agar-agar medium and the mushroom inoculum. This film separates the mushroom from the medium and it is characterized in that the mushroom may feed itself through the film surface. Once the mycelium has invaded the whole surface of the growing medium, the film is withdrawn and dipped into a liquid rich in vitamins and micro-elements. The mycelium and the conidia free themselves from the cellophane film. The mycelium, conidia, vitamins and micro-elements are then lyophilized altogether. The presence of vitamins and micro-elements will help the start on soil.

This technique is original in that the fungal fraction is previously separated from the feeding medium used for its growth. The freeze-dried mushroom is thus in a powder form, water soluble and therefore easier to use for the farmer. The mushroom may be used in this form by mechanical spreading, as any chemicals. With this method, the product quantities to spread on soil are considerably reduced and the product is better and longer preserved. Because of the length of time required to reach the growth apex, mushroom *Arthrobotrys conoides* is preferably blended to the soil to be treated about 15 days before planting.

The efficiency of different strains of *Arthrobotrys conoides* in combating *Meloidogyne, Heterodera* and *Ditylenchus myceliophagus* was first tested in vitro, on Petri plates. For these tests in vitro, the different strains of *Arthrobotrys conoides* were grown on an agar-agar medium (corn meal agar: 1, agar-agar: 1) on Petri plates. Once the mushroom has invaded all the agar-agar, 200 nematodes are aseptically deposited on each plate of mushroom, including on the reference plates, only containing the agar-agar medium. After a period of time of 1 hour, 2 hours, 8 and 24 hours, the plates are turned upside down over a 100 $\mu$m meshed sieve, which bottom comes to the surface of water contained in another Petri plate underneath. With this setting, the nematodes which are not trapped by the mushroom actively go through the sieve to reach the water. The nematodes are then trapped and counted under microscope.

In case of *Meloidogyne* and *Ditylenchus myceliophagus*, the six strains split in two groups: strains A, A' and B trap between 60 and 100% nematodes in 24 hours, the three other strains are less efficient.

In case of *Heterodera carotae*, the six strains trap between 50 and 75% nematodes in 24 hours.

Otherwise, it was observed that the mushroom development was rapid (on average, 1,5 cm per 24 hours). It can thus be used practically and with satisfactory results as a nematophagous agent for farming and floral cultures, as well as for plants in tree nurseries.

Within the framework of tests related to the ecology of the new strains of nematophagous mushroom, it was observed that the latter develops well in soils which salinity does not exceed 3 g/l.

Otherwise, it was noted that the invasion of the medium by the nematophagous mushroom is much more intense when it is blended at a high dose. Yet, the mushroom will noticeably colonize the substrata, even at the dose of 10% in volume of soil.

The predatory activity of the different strains of *Arthrobotys conoides* 42 is confirmed by a number of practical tests, which results are next recalled for information.

I. Tubes testing under glass against *Meloidogyne*

The strains studied are divided in two categories depending on their trapping capacity: on average, A, A' and B trap 80% nematodes per 24 hours; Br, T and Vl only trap 30% *Meloidogyne* per 24 hours.

To realize the testing, the most representative strain of each category was selected, that is to say A and Vl. The testing was conducted in 50 ml tubes containing 30 ml soil. Strains of mushrooms grown on a sterilized, cooked and crushed corn-based medium, were blended to the soil in the proportion of 100 g/m$^2$.

The tubes were treated as follows:

| | |
|---|---|
| Reference tube | soil with no predatory mushroom |
| A1 | soil containing strain A, the infection with nematodes done on the day of blending the mushroom to the soil |
| Vl 1 | soil containing strain Vl, the infection with nematodes done on the day of blending the mushroom to the soil |
| A15 | soil containing strain A, the infection with nematodes done 15 days after blending the mushroom to the soil |
| Vl 15 | soil containing strain Vl, the infection with nematodes done 15 days after blending the mushroom to the soil |
| A1 + Vl 15 | strain Vl blended (half dose: 50 g/m$^2$) to the soil 15 days before the nematodes infection, and strain A on the same day as nematodes, in half dose |

On D day, 30 *Meloidogyne* larva are deposited in each tube. After 24 hours, the tubes of each series are taken out and their contents analyzed, to determine how many nematodes are trapped. This experiment is repeated every day until all nematodes are trapped.

The results are presented in the next table and show that, for any *Arthrobotrys conoides* strain, when the mushroom is blended 15 days before planting (hence before nematodes activation by its host plant), the trapping rate considerably varies for the first days, but this difference rapidly decreases.

| | mean % of trapped nematodes at D + 1 | mean % of trapped nematodes at D + 1 | mean % of trapped nematodes at D + 1 |
|---|---|---|---|
| A1 | 46,14 | 66,67 | 90,28 |
| Vl 1 | 32,09 | 59,44 | 87,22 |
| A15 | 63,12 | 80,28 | 94,44 |
| Vl 15 | 61,8 | 86,11 | 93,06 |
| A1 + Vl 15 | 44,92 | 88,89 | 95,06 |

II. Mini-pots testing under glass against *Meloidogyne hapla*

This testing aims at revealing the action of the mushroom *Arthrobotrys conoides* on the nematode *Meloidogyne hapla*, and at specifying the quantity of product to use per m$^2$. The six strains of *Arthrobotrys conoides* were tested with this nematode. The experiment was conducted in mini-pots containing 300 g soil, the plant selected was a Saint Pierre tomato, a very nematode-sensitive plant.

Each pot was infected with 100 nematodes per 100 g of soil, which corresponds to the high limit of a mean field infection.

The reading of the results reading was realized by coloring the roots with eosin. This vital coloration helps counting the masses of eggs of the first generation, issued from infecting larva which penetrated the radicular system.

*Arthrobotrys conoides* is a predatory mushroom which can survive in the soil when no nematodes are present by digesting organic compounds (saprophagous feeding). That is the reason why a sterile organic enriching agent (without micro-organisms) is added to the station sterile soil. It helps for a better development of the mushroom during the first 15 days of experiment.

Calculation of treatment doses: the base is a number of propagation units equivalent to 10$^8$ propagation units/m$^2$ of soil. For the six *Arthrobotrys conoides* strains, this number is reached on average with 15 g of the autoclaved, crushed corn-based preparation. To have room to maneuver, the mean common dose tested on the six strains was 40 g/m$^2$, and the second dose was double this one, that is to say 80 g/m$^2$. Five repetitions were prepared for each strain and each dose, not forgetting the reference subject, without mushroom.

Results: for the mean dose common to the six strains and corresponding to 40 g/m2, results are as follows:

| | A | A' | B | Br | T | Vl | Ref |
|---|---|---|---|---|---|---|---|
| Nb mass of eggs/plant | 65 | 150 | 145 | 150 | 125 | 123 | 163 |
| % mushroom efficiency | 60% | 8% | 11% | 8% | 23% | 24% | |

Strain A yields the best results.

With a double dose of 80 g/m2, results were as follows:

|  | 2A | 2A' | 2B | 2Br | 2T | 2Vl | Ref |
|---|---|---|---|---|---|---|---|
| Nb mass of eggs/plant | 32 | 116 | 133 | 146 | 94 | 77 | 163 |
| % mushroom efficiency | 80% | 28% | 18% | 10% | 42% | 53% | |

As for the dose of 40 g/m$^2$, strain A yields the best results, but strain Vl is also efficient at this dose. To obtain rapid and reliable results, it is better to use strain A with the dose of 80 g/m2 when this one is grown on a cooked and crushed corn-based medium.

III. Pot testing on a carrot culture attacked with *Heterodera carotae*

This experiment was realized using strains A, B, T and Vl. To prepare this testing, the different strains were grown on a cooked and crushed corn-based substrate. The mushroom quantities brought in were rigorously fitted to each strain so that there is always the same number of propagation units per liter soil (10$^8$ propagation units/100 1). For A and B strains, the inoculation dose was 60 g/100 1 soil. For strain T, the inoculation dose was 190 g/100 1 soil. At last, for Vl strain, the inoculation dose was 80 g/100 1 soil. A carrot culture was kept untreated to stand as reference subject.

During this experiment, the number of *Heterodera carotae* cysts issued from the infecting larva generation was counted.

|  | A | B | T | Vl | Ref |
|---|---|---|---|---|---|
| Cyst number | 39 | 49 | 96 | 40 | 106 |
| % mushroom efficiency | 63% | 54% | 9% | 62% | |

It should be noted that strains A and Vl yield the best results with *Heterodera carotae*, as with *Meloidogyne halpa*.

IV. Testing on tomato culture under glass

This experiment was realized with *Arthrobotrys conoides* 42A under glass, in a farming environment. It aims at specifying the required dose of predatory mushroom to spread on the ground.

For this testing, the mushroom is grown on a crushed corn-based medium. The content of this medium is 10$^7$ propagation units per gram.

The plot of land put at our disposal is 120 m$^2$ big. It was divided into three areas, each 40m$^2$ big, which are separated by means of planks, for a better isolation. The first plot is a reference subject, an area next to it is treated with 50 g/m$^2$ preparation of strain 42A, and the last plot is treated with a 100 g/m$^2$ preparation.

Before setting up the testing, the soil taken between the current cultures (salad) is analyzed.

This was made by planting young sensitive tomato plants (Saint Pierre variety) in the soil to reveal the presence of nematodes. One month after planting, the roots are colored with methyl-blue lactophenol (GUIRAN, 1966). This coloring shows the young *Meloidogyne* which have penetrated the tomato roots.

We found 620 *Meloidogyne* larva per 10 g roots, corresponding to an average infection.

This mean infection rate is perfect for testing the nematophagous mushroom. Indeed, the mushroom acts very slowly, as all biological means of combat, and cannot regulate a too high proliferation of nematodes in only one cultivation campaign.

*Arthrobotrys conoides* 42A was spread 15 days before planting the tomatoes. This period of 15 days offers to the predatory mushroom the opportunity of colonizing the soil and thus be operational at planting time. Indeed, the tomato plants produce in the ground some root exsudates which help leading the young larva to the roots.

The tomato plants are distributed on four rows, in the two medium rows (to avoid edge effects), 10 sensitive tomato plants (variety Saint Pierre) are planted. These are the ones that will be pulled out for analysis.

Samples were last taken at the end of the culture. The sensitive plants were pulled out and their roots analyzed.

To do so, once the radicular system has been washed, it is crushed in a 1% solution of calcium hypochlorite, at 12˙ chlorometric. This mixture goes through a series of sieves to discard the fragments of vegetal tissues. The *Meloidogyne* eggs issued from the root are collected on a 5 μm meshed sieve and counted under microscope. They constitute the infesting potential of the culture to come.

|  | Ref plot | 50 g/m$^2$ plot | 100 g/m$^2$ plot |
|---|---|---|---|
| Nb eggs per 10 g of roots | 44 581 | 25 838 | 17 725 |

Some points should be specified:

a *Meloidogyne* female can lay 300 to 500 eggs depending on the weather conditions.

an infection is considered as a mean infection when the number of larva per 10 g roots is between 100 and 1000.

The decrease of the infesting potential ( more than half) is noticeable between the reference plot and the plot treated with 100 g/m$^2$ *Arthrobotrys conoides* 42A.

For the plants which are delivered with lumps, pots or containers, the nematophagous mushroom is directly blended to the lump, pot or container.

The predatory mushroom is seeded at the beginning, in the pressed lumps used for market plants. With such a method, it appears that within the 20 to 30 days during which the plants freshly picked out in the lumps are grown in greenhouses in a warm and humid environment, the mushroom grows and invades the whole lump, then behaving as an inoculum, once planted in cultures. This variant of the invention, applicable to plants delivered with lumps, pots, containers or anything alike, presents the following decisive advantages:

Usually, to prepare lumps, a humus rich soil, with a neutral pH, is used, and it particularly favors the development of *Arthrobotrys conoides* 42. Moreover, it was observed that the plant radicular system is completely enveloped in the mycelian felting, yet the latter does not at all disturb its growth. The radicular system is thus protected against nematodes, even when the lump is planted in an strongly infested soil. In this way, the young plant is protected as soon as the vegetation starts, through the period when the plant is the most vulnerable to nematode attacks.

The different experiments proved that the lump makes an important inoculum, from which the mushroom will very easily spread to the surrounding soil.

The preparation of such lumps, pots, containers or anything alike does not raise any difficulty, nor in the use, neither in the preparation of the plants. There is just to put the granule in the soil mix, for example using a hopper. The planting of plants prepared with such a method is achieved as usual.

To sum up, the process of the invention may be applied to any market gardening, floral cultures, or to plants for tree nurseries, though some of them are not sensitive to *Meloidogyne* nematodes. It may also be used to treat carrot cultures, which are sensitive to *Heterodera carotae*, or against *Ditylenchus myceliophagus* in the case of the cultivated mushrooms *Agaricus Bisporus*. In the latter case, the nematophagous mushroom is added to the compost after pasteurization.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

A T G G A T C C G C        1 0

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

T G A C C C T C C A  A G A A G G T        1 7

I claim:

1. A nematophagous agent to combat nematodes of the *Meloidogyne, Heterodera* and *Ditylenchus* genus, wherein the nematophagous agent is selected from the group consisting of one of five isolated strains of *Arthrobotrys conoides* Dreschsler deposited at the National Collection of Micro-organism Cultures respectively under accession numbers: I-1425, I-1426, I-1428, I-1429, I-1430.

2. A process to combat *Meloidogyne, Heterodera* and *Ditylenchus myceliophagus* nematodes in soil comprising blending into the soil an effective amount of the nematophagous agent according to claim 1.

3. The process according to claim 2, in which agricultural grains previously coated with an inoculum of the nematophagous agent are blended into the soil.

4. The process according to claim 3, in which said grains are chosen among the group consisting in alpist, lentil and corn.

5. The process according to claim 4, in which the nematophagous agent is previously seeded in a crushed corn-based medium, containing at least $10^7$ propagation units of the nematophagous agent per gram of said corn-based medium.

6. The process according to claim 4, in which the nematophagous agent is seeded in a crushed, cooked and sterilized corn-based medium, said medium being then blended into the soil, in the proportion of 80 g per square meter of soil.

7. The process according to claim 4, in which the nematophagous agent is seeded in a crushed, cooked and sterilized corn-based medium, said medium being then blended into the soil, in the proportion of 2 g per liter of soil.

8. The process according to claim 2, in which the nematophagous agent is freeze-dried before being blended in powder form with the soil.

9. The process according to claim 3, in which the nematophagous agent is grown on a culture medium so that the conidia develop before freeze-drying.

10. The process according to claim 9, in which a cellophane film is inserted between the growing nematophagous agent and the culture medium, so that the parts of said nematophagous agent containing the conidia are collected by dipping said cellophane film in a liquid in order to free said nematophagous agent from said cellophane film.

11. The process according to claim 2, in which the nematophagous agent is directly blended into a soil of a lump, pot or container used to deliver plants.

12. The process according to claim 2, in which said nematophagous agent is blended with the soil at least fifteen days before planting a desired agricultural product in said soil.

\* \* \* \* \*